(12) United States Patent
Fang et al.

(10) Patent No.: US 8,261,428 B2
(45) Date of Patent: Sep. 11, 2012

(54) METHOD FOR ASSEMBLING A 3-DIMENSIONAL MICROELECTRODE STRUCTURE

(75) Inventors: Weileun Fang, Hsinchu (TW); Yu-Tao Lee, Hsinchu (TW); Yen-Chung Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 287 days.

(21) Appl. No.: 12/626,303

(22) Filed: Nov. 25, 2009

(65) Prior Publication Data

US 2011/0125001 A1 May 26, 2011

(51) Int. Cl.
*G01R 3/00* (2006.01)
(52) U.S. Cl. .......... 29/595; 29/592.1; 29/609.1; 29/831; 29/846; 73/504.04; 73/504.12; 73/504.15; 73/504.16; 310/330; 310/332; 310/340; 310/344; 310/345; 600/372; 600/373
(58) Field of Classification Search .................. 29/592.1, 29/594, 595, 609.1, 831, 846; 73/504.04, 73/504.12–504.16; 310/330–332, 340, 344, 310/345; 600/372, 373
See application file for complete search history.

(56) References Cited

U.S. PATENT DOCUMENTS

| | | | | |
|---|---|---|---|---|
| 4,061,969 A * | 12/1977 | Dean | ......................... | 324/756.07 |
| 6,951,119 B1 | 10/2005 | Quenzer et al. | | |
| 6,993,392 B2 * | 1/2006 | Nicolelis et al. | ................. | 607/45 |
| 7,212,851 B2 * | 5/2007 | Donoghue et al. | ............. | 600/544 |
| 7,259,080 B2 | 8/2007 | Quenzer et al. | | |
| 7,946,050 B2 * | 5/2011 | Chiou et al. | ..................... | 33/557 |

OTHER PUBLICATIONS

Campbell et al., "A Silicon-Based, Three-Dimensional Neural Interface: Manufacturing Processes for an Intracortical Electrode Array," IEEE Transactions on Biomedical Engineering, 1991, pp. 758-768, vol. 38.
Takeuchi et al., "3D flexible multichannel neural probe array," Journal of Micromechanics and Microengineering, 2004, pp. 104-107, vol. 14.
Bai et al., "A High-Yield Microassembly Structure for Three-Dimensional Microelectrode Arrays," IEEE Transactions on Biomedical Engineering, 2000, pp. 281-289, vol. 47.

* cited by examiner

*Primary Examiner* — Paul D Kim
(74) *Attorney, Agent, or Firm* — Muncy, Geissler, Olds & Lowe, PLLC (57) ABSTRACT

The present invention discloses a method for assembling a 3D microelectrode structure. Firstly, 2D microelectrode arrays are stacked to form a 3D microelectrode array via an auxiliary tool. Then, the 3D microelectrode array is assembled to a carrier chip to form a 3D microelectrode structure. The present invention uses an identical auxiliary tool to assemble various types of 2D microelectrode arrays having different shapes of probes to the same carrier chip. Therefore, the method of the present invention increases the design flexibility of probes. The present invention also discloses a 3D microelectrode structure, which is fabricated according to the method of the present invention and used to perform 3D measurement of biological tissues.

9 Claims, 12 Drawing Sheets

METHOD FOR ASSEMBLING A 3-DIMENSIONAL MICROELECTRODE STRUCTURE

FIELD OF THE INVENTION

The present invention relates to a 3D microelectrode structure, particularly to a 3D microelectrode structure for physiological signal measurement. The present invention also relates to a method for assembling a 3D microelectrode structure, particularly to a method for assembling a 3D microelectrode structure, which can align accurately and assemble easily.

BACKGROUND OF THE INVENTION

Since a planar multi-electrode array was proposed to study the transmission mechanism of neural signals in 1972, microelectrode arrays have been extensively used in the biomedical engineering. Taking the signal measurement of the nervous system for an example, the brain and a neural network is a complicated network consisting of many neurons interconnecting each other. Understanding the operation of the neural network is very important to diagnose and treat neural diseases, and even fabricate neural prostheses. A probe can easily insert into the tissue to research the variations of the electrophysiological signals in vivo.

The early study of neural signal transmission is mainly implemented by a single electrode probe, such as a metal probe or a glass micropipette. However, such an electrode probe is bulky and likely to be interfered. Further, the single electrode probe can only record a single or few nerve cells at the same time. Recently, the MEMS (Micro-Electro-Mechanical System) or semiconductor manufacturing process has implemented a microelectrode array containing multiple micron-scale probes, whereby a higher number of nerve cells can be measured. The photolithography technology of the semiconductor manufacturing process can precisely define the positions of electrodes. Further, the abovementioned processes can easily integrate the circuits. However, the abovementioned processes usually fabricate the microelectrodes into a planar microelectrode array, which has limited application in the 3D biological tissues.

There are mainly three conventional methods to fabricate 3D microelectrode arrays. One method uses photolithography and etching technologies to directly fabricate a microelectrode array on a silicon wafer. For example, R. A. Normann et al. disclosed "A Silicon-Based, Three-Dimensional Neural Interface: Manufacturing Processes for an Intracortical Electrode Array" in IEEE Transactions on Biomedical Engineering, vol. 38, pp. 758-768, 1991. Such a device is also called the "Utah Array". However, the thickness of the wafer limits the length of the probes to adjust freely. Further, each probe has only an electrode, which limits the recording density. Besides, the biocompatibility of silicon is not as good as other material (e.g. polymer, ceramic, and glass).

A second method uses a self-assembly technology to form a 3D microelectrode array. For example, Shoji Takeuchi et al. disclosed "3D Flexible Multichannel Neural Probe Array" in Journal of Micromechanics and Microengineering, vol. 14, pp. 104-107, 2004, wherein a magnetic material is coated on planar polymer arrays, and then the flexible polymer probes are assembled with the magnetic force to form a 3D array structure. However, the structural strength of such a mircoprobe is hard to control. Further, the magnetic material may have adverse effect to the organism.

A third method assembles 2D planar microprobe arrays into a 3D microprobe array. For example, the research team led by Wise of Michigan University discloses "A High-Yield Microassembly Structure for Three-Dimensional Microelectrode Arrays" in IEEE Transactions on Biomedical Engineering, vol. 47, pp. 281-289, 2000, wherein planar microelectrode arrays are separated by spacers and inserted into slots of a silicon platform to form a 3D structure. However, such a device is complicated, and the orthogonality thereof is hard to control.

The conventional methods that assemble planar microelectrode arrays into a 3D microelectrode array have the advantages of increasing electrode design flexibility, promoting efficiency of recording electroneurographic signals, and implementing space analysis. However, the conventional methods for assembling 3D microelectrode arrays have the disadvantages of inconvenient assembly. Further, the conventional 3D microelectrode arrays still have room to improve in biocompatibility.

SUMMARY OF THE INVENTION

One objective of the present invention is to provide a method for assembling a 3D microelectrode structure, whereby the 3D microelectrode array and the carrier chip have better electric connection, and whereby the 3D microelectrode structure is easy to assemble and has accurate alignment.

To achieve the abovementioned objective, the present invention proposes a method for assembling a 3D microelectrode structure, which comprises the steps of: fabricating 2D microelectrode arrays, wherein each 2D microelectrode array has a base, a plurality of probes connected to the base and a plurality of alignment members connected to the base, and wherein the probe has at least one electrode electrically connected to the alignment member via a corresponding wire; stacking the 2D microelectrode arrays into a 3D microelectrode array and aligning the alignment members of the 2D microelectrode arrays to the predetermined positions; assembling the 3D microelectrode array to a carrier chip to form a 3D microelectrode structure with each alignment member electrically connected to the corresponding electric-connection pad of the carrier chip.

Another objective of the present invention is to provide a 3D microelectrode structure, which is fabricated according to the abovementioned method, and which can simultaneously measure many physiological signals, and which has the advantages of high measurement density, high insertion capability, great insertion depths, flexible probe/electrode arrangement, and high biocompatibility.

Below, the embodiments will be described in detail in cooperation with the drawings to demonstrate the technical contents of the present invention.

BRIEF DESCRIPTION OF THE DRAWINGS

The embodiments of the present invention will be described in detail in cooperation with the following drawings.

DETAILED DESCRIPTION OF THE PREFERRED EMBODIMENT

Figure 1:
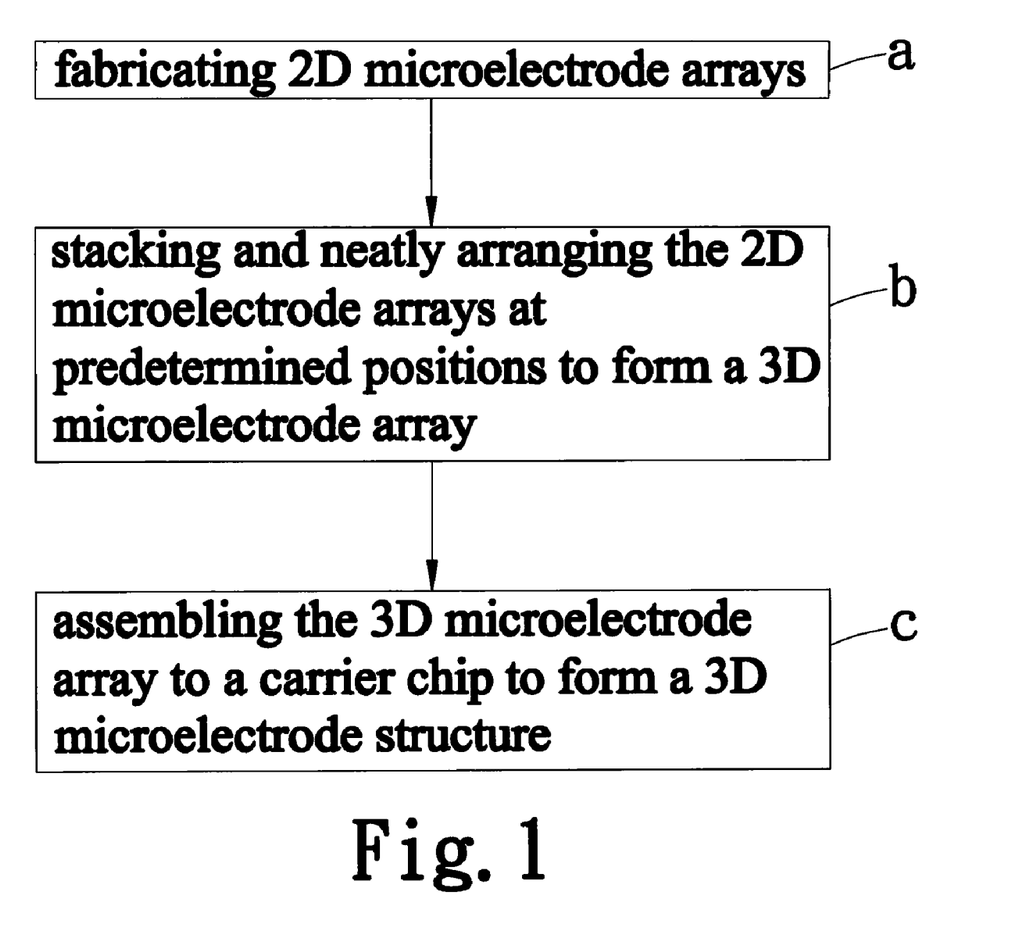
FIG. 1 is a flowchart of a method for assembling a 3D microelectrode structure according to the present invention.

Refer to FIG. 1 for a flowchart of a method for assembling a 3D microelectrode structure according to the present invention. The method for assembling a 3D microelectrode structure of the present invention comprises the steps of:

a. fabricating 2D microelectrode arrays;
b. stacking and neatly arranging the 2D microelectrode arrays at predetermined positions to form a 3D microelectrode array;
c. assembling the 3D microelectrode array to a carrier chip to form a 3D microelectrode structure.

Below, the steps are described in detail.

Figure 2:
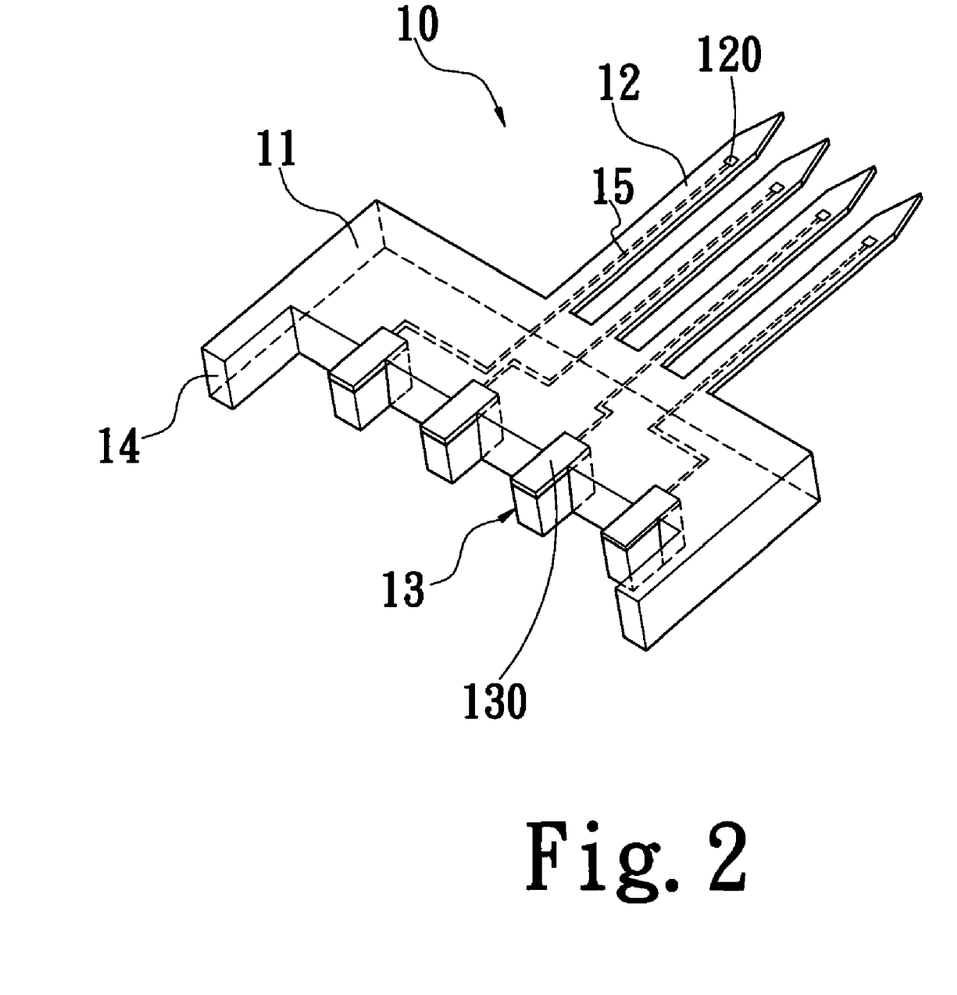
FIG. 2 is a perspective view of the appearance of a 2D microelectrode array according to one embodiment of the present invention.

In Step a, a 2D microelectrode array 10 is fabricated. Refer to FIG. 2 for an embodiment of a 2D microelectrode array 10 according to the present invention. The 2D microelectrode array 10 comprises a base 11, a plurality of probes 12 connected to the base 11, a plurality of alignment members 13 connected to the base 11, and a plurality of positioning members 14 connected to the base 11. The probes 12 and the alignment members 13 are respectively located at different sides of the base 11. Each alignment member 13 has an exposed electric-connection member 130. Each probe 12 has at least one electrode 120. The electrodes 120 are respectively electrically connected to the corresponding electric-connection member 130 via wires 15. The wires 15 are electrically insulated to each other. The wires 15 are wrapped inside the probes 12 and the base 11 lest the wires 15 electrical short to the body fluid. In this embodiment, the alignment members 13 and the positioning members 14 are located at the same side of the base 11.

Considering the biocompatibility with organisms, the 2D microelectrode array 10, especially the base 11 and probe 12, are made of a high biocompatibility material, such as a glass, PDMS (Polydimethylsiloxane), PI (polyimide), or a thick SU-8 photoresist. Considering the influence of material strength on the insertion depth, the 2D microelectrode array 10 is made of a glass and fabricated with a glass reflow technology in one embodiment. However, the present invention is not limited by this embodiment. As the glass reflow technology is a prior art, it will not repeat herein. For the details of the glass reflow technology, please refer to an U.S. Pat. No. 7,259,080 "Glass-type Planar Substrate, Use Thereof, and Method for the Production Thereof", and an U.S. Pat. No. 6,951,119 "Method for producing micromechanical and micro-optic components consisting of glass-type materials".

Figure 3A:
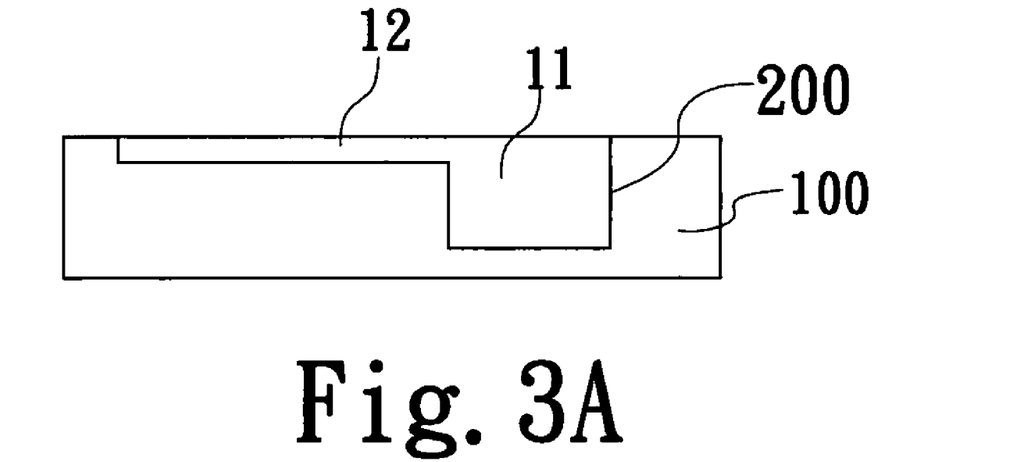
FIGS. 3A-3D are diagrams schematically showing the process of fabricating a 2D microelectrode array according to one embodiment of the present invention.
Figure 3B:
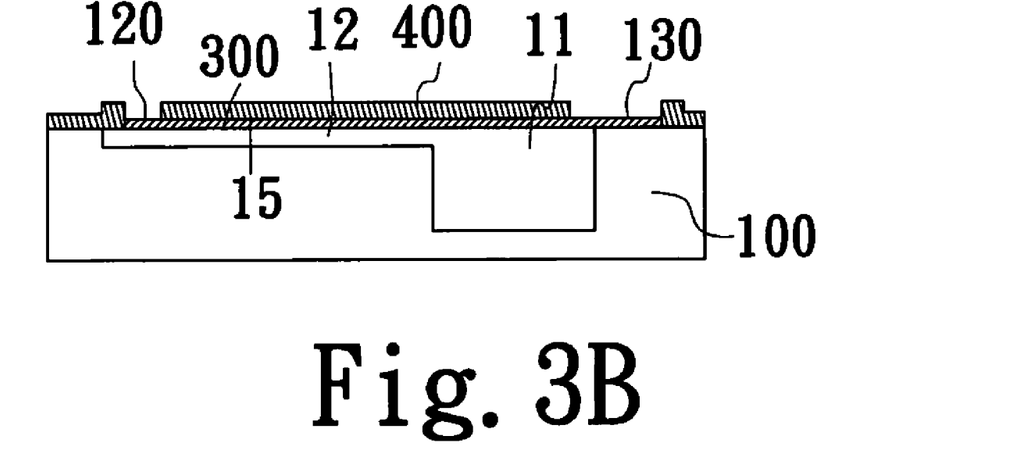
Figure 3C:
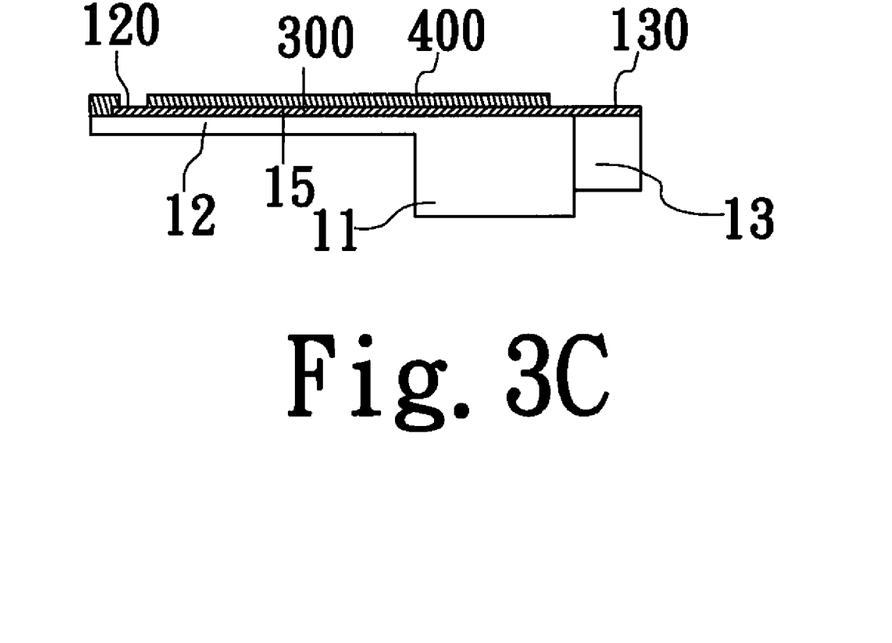
Figure 3D:
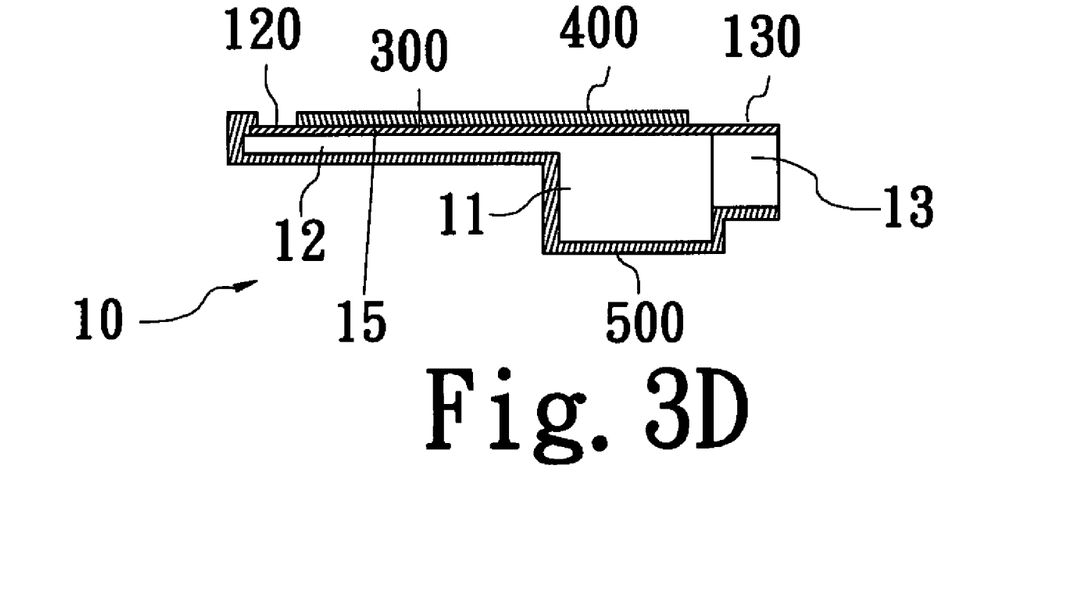

Refer to FIGS. 3A-3D for diagrams schematically showing the process of fabricating a 2D microelectrode array 10 according to the present invention. As shown in FIG. 3A, a master mold 200 is formed on a silicon wafer 100 firstly; then, molten glass is cast into the master mold 200 via a glass reflow technology; then, the undesired portions are removed via lapping; thus is formed the rough structure of the base 11 plus the probes 12. Next, as shown in FIG. 3B, a metal film 300 and an insulating film 400 are deposited to define the electrodes 120, the wires 15 and the electric-connection members 130 of the 2D microelectrode array 10. The insulating film 400 is made of an insulating material, such as silicon dioxide, silicon nitride, or Parylene. Next, as shown in FIG. 3C, the undesired silicon structure is removed by etching, and the thickness of the silicon structure of the alignment members 13 is defined at the same time. Next, as shown in FIG. 3D, an adhesive layer 500 is deposited on the predetermined position. The adhesive layer 500 may be made of Parylene-C. Thus is completed the 2D microelectrode array 10. Refer to FIG. 2 again. In the abovementioned embodiment, the metal film 300 is located on the probe 12 and is exposed from the insulating silicon dioxide film 400 to be defined the electrode 120; the metal film 300, which is exposed from the alignment member 13, is defined to be the electric-connection member 130.

It should be understood that the process of fabricating a 2D probe 12 array described in the abovementioned embodiments is only an exemplification of the present invention. In practical applications, the electrode 120, wire 15, and electric-connection member 130 may be made of different material according to the characteristics and requirements, such as the electrode 120 can be selected from a group consisting of CNT (Carbon Nano-Tubes), iridium oxide, platinum, gold, titanium, platinum black, or an electric-conduction polymer PEDOT (polyethylenedioxythiophene). Further, the base 11, probes 12, alignment members 13 and positioning members 14 mentioned in the embodiments may be fabricated into independent parts or a one-piece component.

In Step b, the 2D microelectrode arrays 10 are stacked and neatly arranged to form a 3D microelectrode array 30. Refer to FIGS. 4A-4E for diagrams schematically showing the procedures of Step b according to one embodiment of the present invention. In this embodiment, an auxiliary tool 20 is used to arrange the alignment members 13 of the 2D microelectrode arrays 10 neatly at the predetermined positions, whereby the 2D microelectrode arrays 10 are stacked to form a 3D microelectrode array 30.

Figure 4A:
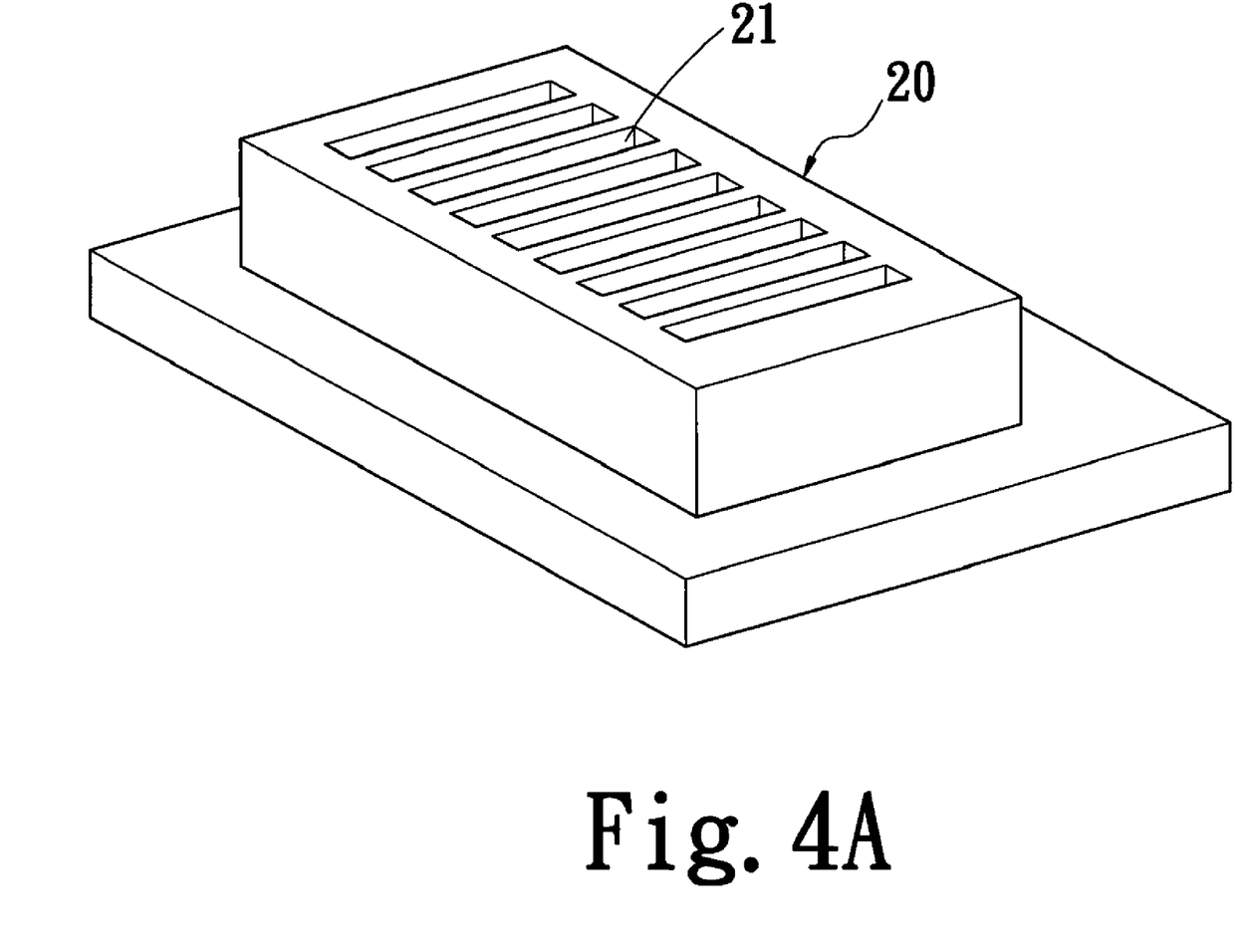
FIGS. 4A to 4E are diagrams schematically showing the procedures of Step b according to one embodiment of the present invention.
Figure 4B:
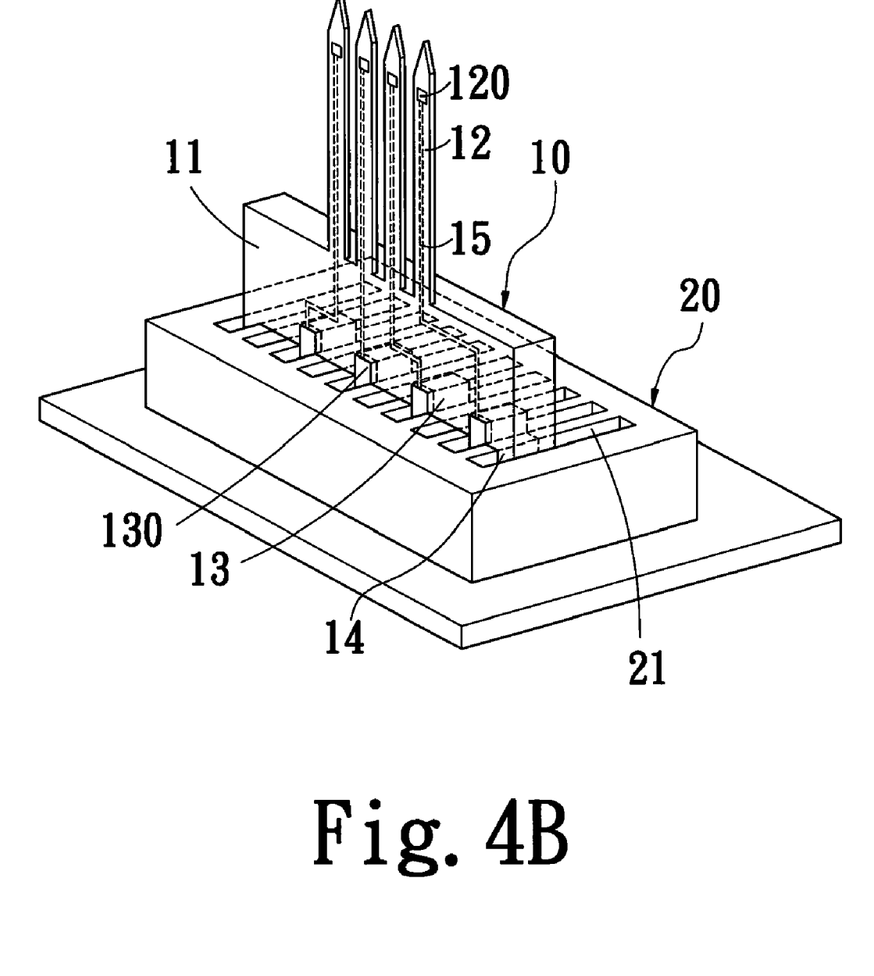

As shown in FIGS. 4A and 4B, the auxiliary tool 20 has a plurality of slots 21 arranged in parallel. The slots 21 accommodate the alignment members 13 and the positioning members 14, enable the 2D microelectrode arrays 10 to slide along the direction parallel to the slots 21, and align the corresponding 2D microelectrode arrays 10. The width of each slot 21 and the spacing between two adjacent slots 21 are not strictly limited. However, considering the positioning effect, the width of each slot 21 is preferred to be slightly greater than the width of the alignment member 13. In one embodiment, the sections of the slots 21 are patterned on a wafer, and the sections are etched to form the auxiliary tool 20.

Figure 4C:
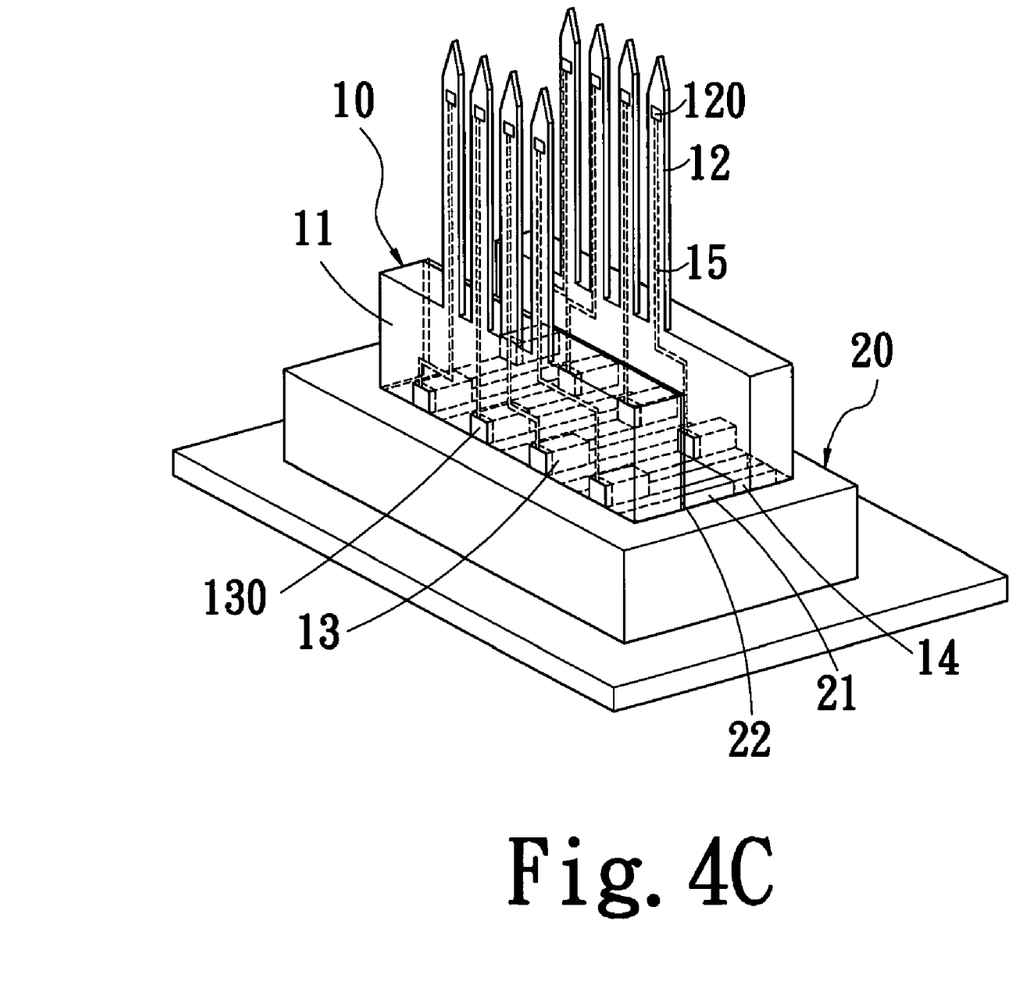
Figure 4D:
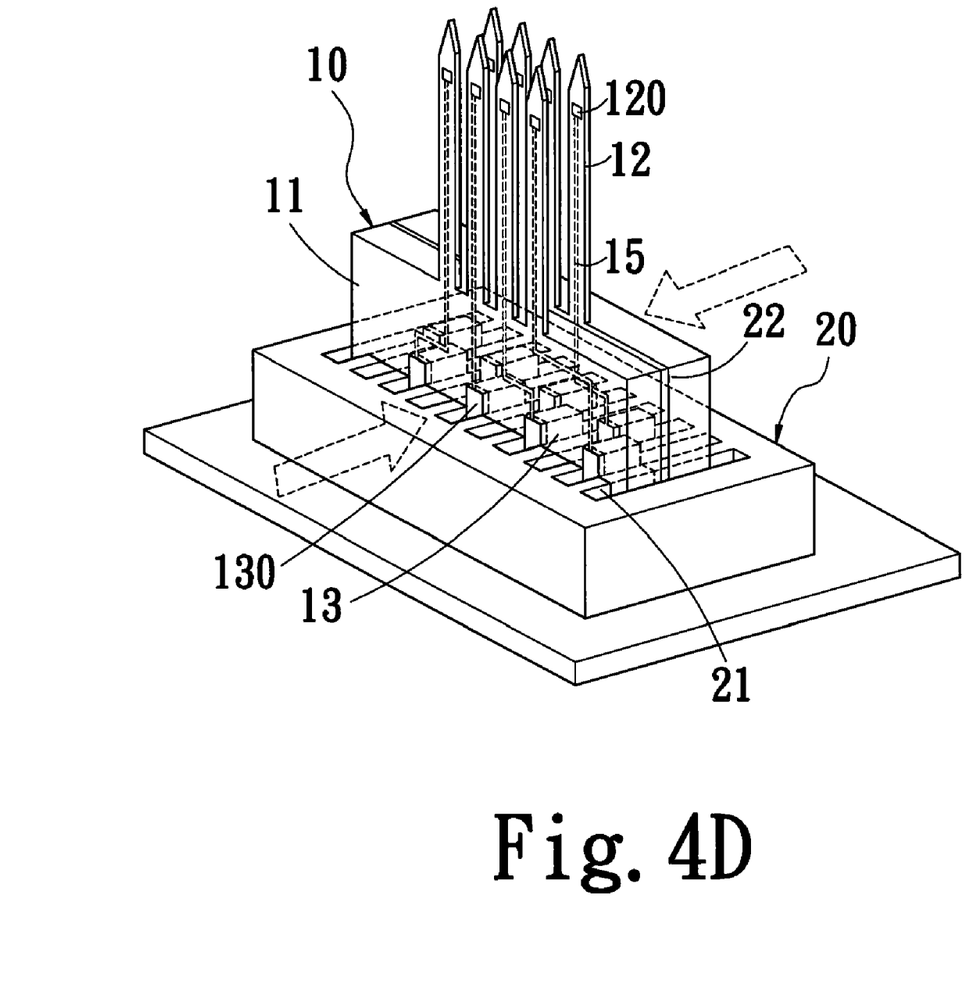
Figure 4E:
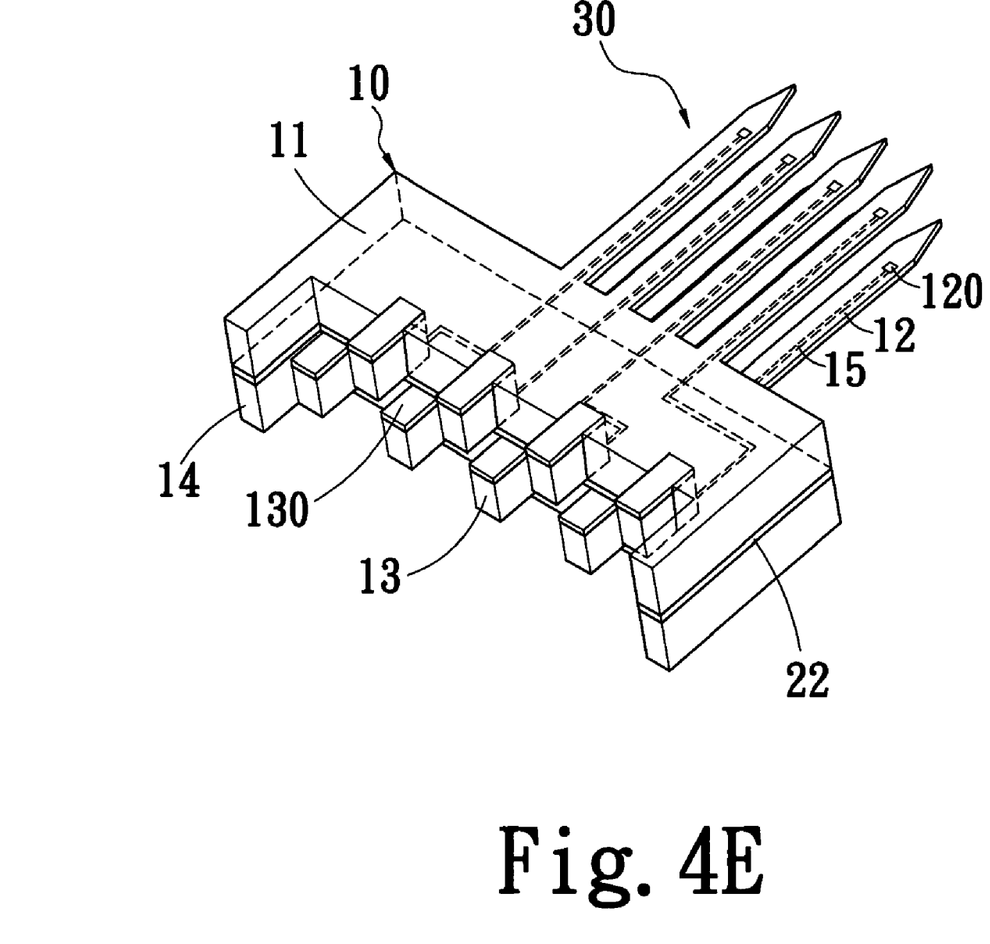

As shown in FIGS. 4C and 4D, a plurality of 2D microelectrode arrays 10 located at the alignment positions of the auxiliary tool 20 is stuck to form a 3D microelectrode array 30 via adhesive layers 22. As shown in FIG. 4E, the alignment members 13 are thus arranged to have a predetermined shape. During the assembling, the positioning and securing effect is enhanced via heating and applying pressure to the 3D microelectrode array 30 along the direction to the slots 21 (indicated by the arrow in FIG. 4D). In one embodiment, Parylene-C is uniformly coated on the contact faces of the bases 11 of the 2D microelectrode arrays 10, and then the 2D microelectrode arrays 10 are pressured and heated to a temperature of 260° C. for 2 hours, whereby forms the 3D microelectrode array 30. As shown in FIG. 4E, the alignment members 13 of different 2D microelectrode arrays 10 are alternately arranged lest interference occurs. However, it should be understood that the present invention does not strictly limit the arrangement of the alignment members 13 of the established 3D microelectrode array 30.

Figure 5A:
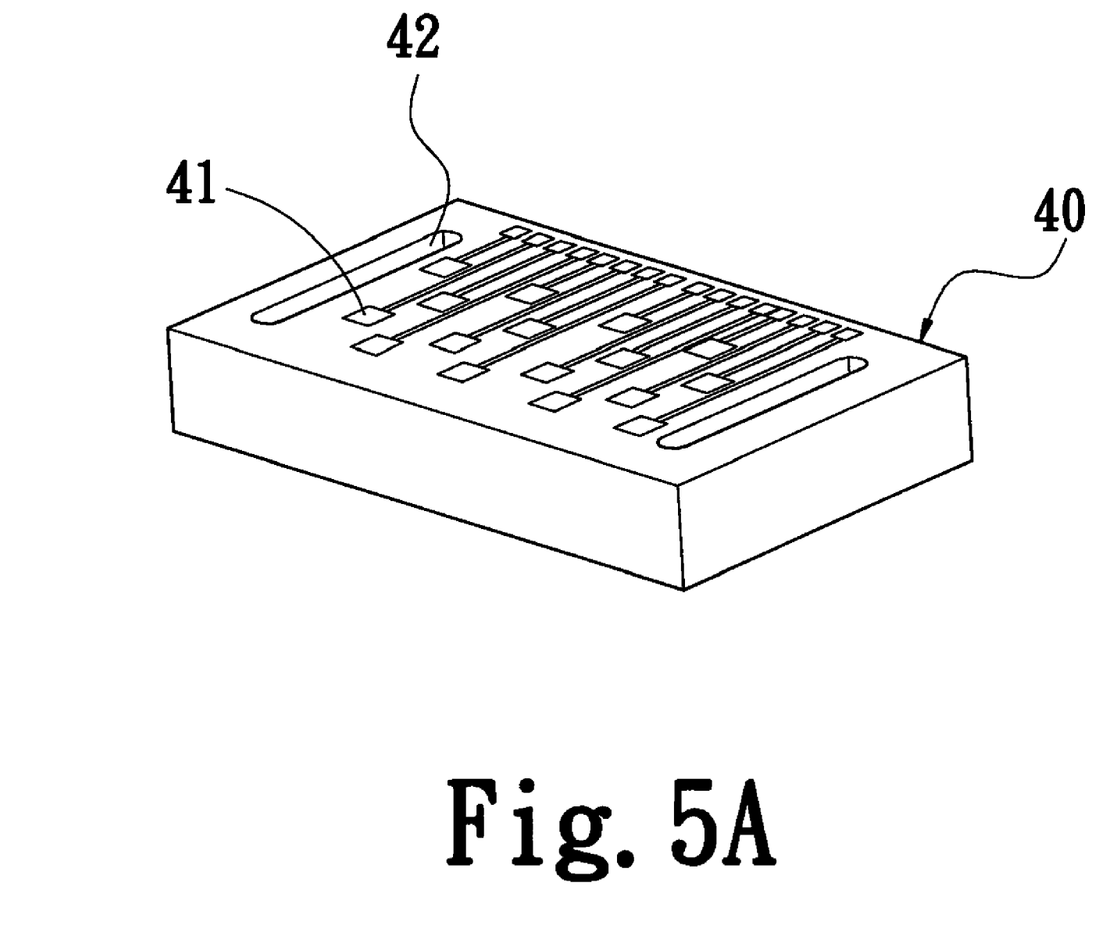
FIG. 5A is a perspective view of the appearance of a carrier chip according to one embodiment of the present invention.
Figure 5B:
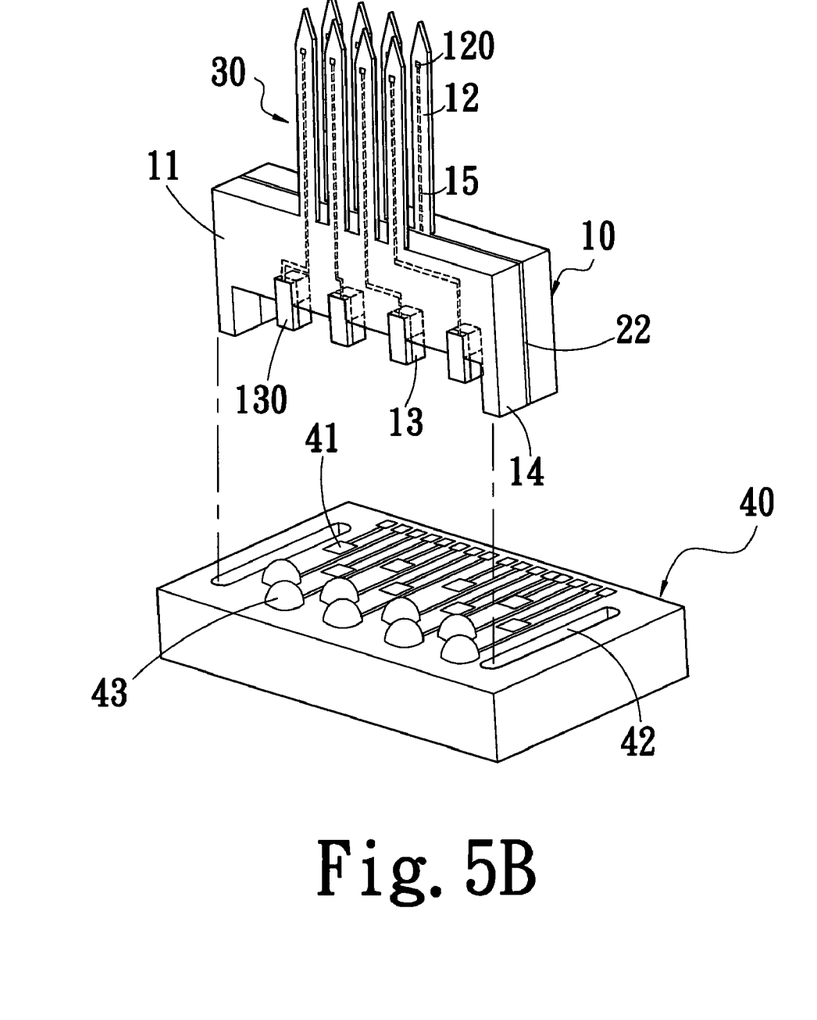
FIG. 5B is a diagram schematically showing the procedures of Step c according to the present invention.
Figure 5C:
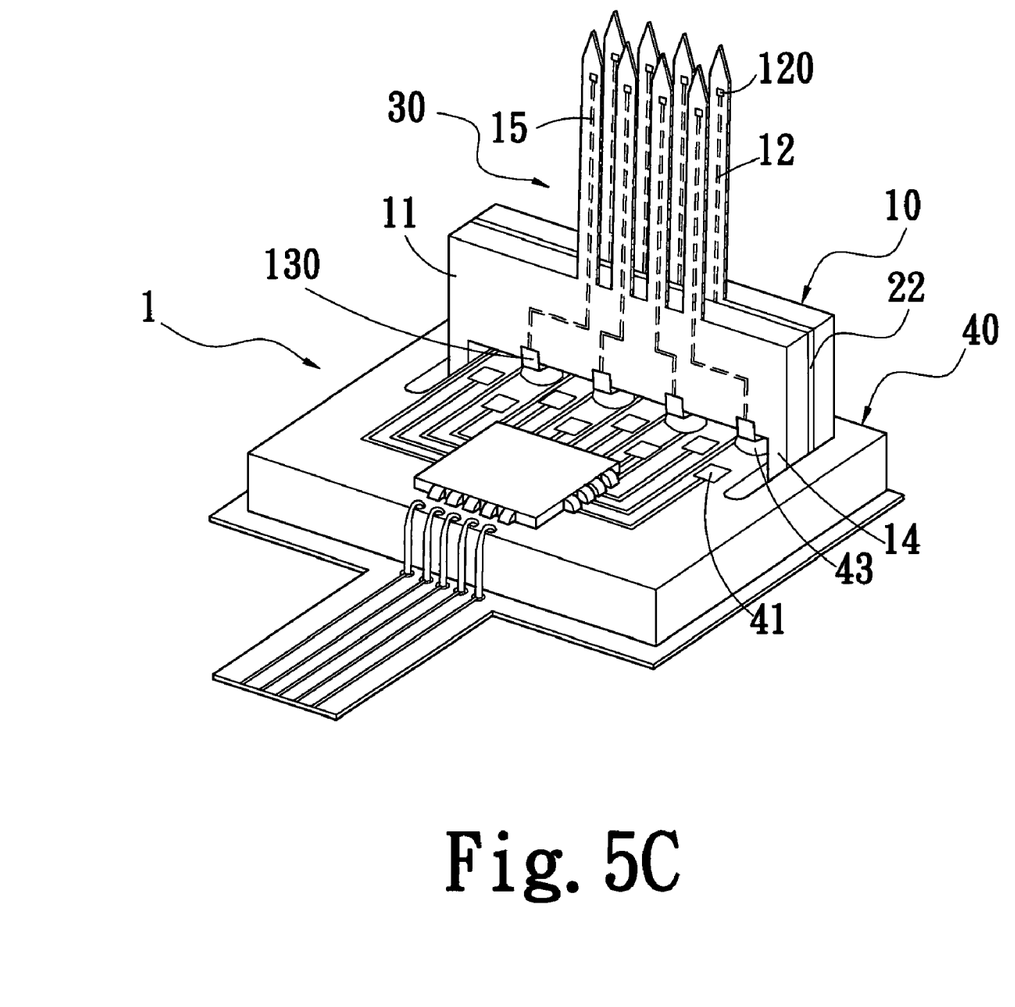
FIG. 5C is a perspective view of the appearance of a 3D microelectrode structure according to the present invention.

In Step c, the 3D microelectrode array 30 is assembled to a carrier chip 40 to form a 3D microelectrode structure 1. Refer to FIGS. 5A and 5B respectively for a diagram schematically showing the appearance of the carrier chip 40 and a diagram schematically showing the procedure of Step c. The carrier chip 40 includes a plurality of electric-connection pads 41 and a plurality of slots 42. The arranged pattern of the electric-connection pads 41 is corresponding to the alignment members 13 of the 3D microelectrode array 30, whereby each exposed electric-connection member 130 of the alignment member 13 can electrically connect to the corresponding electric-connection pad 41. The slots 42 accommodate the positioning members 14 to assist in aligning and securing the 3D microelectrode array 30 to the carrier chip 40. As shown in FIG. 5B, a conductive paste 43 is used as the adhesive and electric-conduction medium when the electric-connection pads 41 contact the electric-connection members 130. In assembling, the positioning members 14 of the 3D microelectrode array 30 are inserted into the slots 42, whereby the alignment members 13 can be aligned to contact the electric-connection pads 41. The conductive paste 43 is heated and solidified to interconnect the electric-connection pads 41 and the electric-connection members 130. The conductive paste 43 may be a silver paste. As shown in FIG. 5C, the 3D microelectrode structure 1 is further integrated with a flexible substrate and an ASIC to perform nervous system measurement.

The alignment of the 2D microelectrode arrays 10 is implemented with the alignment members 13 of the base 11. Different type 2D microelectrode arrays 10 may have different numbers and shapes of probes 12. However, in the present invention, different type 2D microelectrode arrays 10 can be assembled into corresponding 3D microelectrode arrays 30 with the same auxiliary tool 20 or the same carrier chip 40, as long as they have the same type of base 11. Thus is increased the design flexibility and expanded the application of the probe 12. For example, the combinations of the probes 12 having different lengths can be used to measure the physiological signals from different depths of an organism at the same time. Further, as the alignment member 13 has a greater bottom area, the electric-connection member 130 can easily conduct the electric-connection pad 41 in Step c. Thus, the disconnection caused by an alignment error will not occur. It should be understood that the electric-connection member 130 exposed from the alignment member 13 may be a portion of the alignment member 13 or the alignment member 13 itself in fact. In this specification, different terms do not necessarily indicate different entities but may be used to demonstrate different aspects of the same thing.

The present invention also proposes a 3D microelectrode structure 1, which is assembled with the abovementioned method, comprises a carrier chip 40 and a 3D microelectrode array 30 electrically connected to the carrier chip 40, wherein a plurality of 2D microelectrode arrays 10 is stacked to form the 3D microelectrode array 30. The material and detailed structure of the 2D microelectrode array 10 is the same as that described above. The 2D microelectrode arrays 10 are stacked to make the bases 11 thereof contact each other and form the 3D microelectrode array 30. In one embodiment, the probe 12 is made of a glass material and thus has high insertion ability and high biocompatibility. In the present invention, different type 2D microelectrode arrays 10 having different numbers and shapes of probes 12 may adopt the same type of base 11. Therefore, the present invention can easily realize the 3D microelectrode arrays 30 having flexible arrangements and combinations of probes 12, such as a 3D microelectrode arrays 30 having longer probes 12 for a greater insertion depth. In another embodiment, the probes 12 have several electrodes 120 to measure more nerve cells.

The signals of a nervous system are mainly transmitted by neurons. When a neuron is stimulated, special ion channels on the cell membrane is opened. Thus, ions, such as potassium ions and sodium ions, flow through cell membrane and result in potential change. When the potential is accumulated over a threshold, an action potential is generated and detected by the probe 12 in the form of voltage. The 3D microelectrode structure 1 of the present invention has succeeded in measuring and recording the action potential of crayfish nerve cord and rat cortices. The SNR (Signal-to-Noise Ratio) in measuring crayfishes is 32.6 dB, wherein the SNR is defined to be the ratio of the amplitude of the nerve impulse to the root-mean-square value of noise.

The embodiments described above are only to exemplify the present invention but not to limit the scope of the present invention. Any equivalent modification or variation according to the scope of the present invention is to be also included within the scope of the present invention.

What is claimed is:

1. A method for assembling a 3-dimensional microelectrode structure, comprising the steps of:
   Step a: fabricating 2-dimensional microelectrode arrays, wherein each of said 2-dimensional microelectrode arrays includes a base, a plurality of probes, a plurality of alignment members and a plurality of positioning members, and wherein said probes, said alignment members and said positioning members are connected to said base, and wherein each of said probes has at least one electrode, and wherein said at least one electrode is electrically connected to at least one of the plurality of the alignment members via a corresponding wire;
   Step b: stacking said 2-dimensional microelectrode arrays to form a 3-dimensional microelectrode array, wherein said alignment members of said 2-dimensional microelectrode arrays are neatly arranged at predetermined positions; and
   Step c: assembling said 3-dimensional microelectrode array to a carrier chip to form the 3-dimensional microelectrode structure, wherein said alignment members are electrically connected to a plurality of electric-connection pads of said carrier chip correspondingly.

2. The method for assembling a 3-dimensional microelectrode structure according to claim 1, wherein each of the plurality of the alignment members has an exposed electric-connection member; said at least one electrode is connected to corresponding said electric-connection member via the corresponding wire; in said Step c, said electric-connection members are respectively electrically connected to corresponding said electric-connection pads of said carrier chip.

3. The method for assembling a 3-dimensional microelectrode structure according to claim 2, wherein said carrier chip has a plurality of slots; in said Step c, said positioning members are accommodated in said slots, whereby said alignment members are aligned to contact said electric-connection pads, and said electric-connection members are electrically connected to said electric-connection pads.

4. The method for assembling a 3-dimensional microelectrode structure according to claim 1, wherein said 2-dimensional microelectrode arrays are made of a material selected from a group consisting of a glass, PDMS (Polydimethylsiloxane), PI (polyimide), and a thick SU-8 photoresist.

5. The method for assembling a 3-dimensional microelectrode structure according to claim 1, wherein said at least one electrode is made of a material selected from a group consisting of carbon nanotubes, iridium oxide, platinum, gold, titanium, platinum black, and an electric-conduction polymer PEDOT (polyethylenedioxythiophene).

6. The method for assembling a 3-dimensional microelectrode structure according to claim 1, wherein said alignment members are a silicon structure.

7. The method for assembling a 3-dimensional microelectrode structure according to claim 1, wherein said alignment members of different 2-dimensional microelectrode arrays are alternately arranged.

8. The method for assembling a 3-dimensional microelectrode structure according to claim 1, wherein in said Step b, said 2-dimensional microelectrode arrays are stacked to form said 3-dimensional microelectrode array via an auxiliary tool; said auxiliary tool has a plurality of parallel slots; said slots accommodate said alignment members and said positioning members and enables said 2-dimensional microelectrode arrays to slide in said auxiliary tool.

9. The method for assembling a 3-dimensional microelectrode structure according to claim 8, wherein in said Step b, an adhesive layer is applied to bond said 2-dimensional microelectrode arrays; then, pressure is applied to said 2-dimensional microelectrode arrays to form said 3-dimensional microelectrode array.

* * * * *